United States Patent
Kaku

(10) Patent No.: US 10,802,265 B2
(45) Date of Patent: Oct. 13, 2020

(54) ENDOSCOPIC DIAGNOSTIC APPARATUS AND LESION PART VOLUME MEASURING METHOD

(71) Applicant: FUJIFILM Corporation, Tokyo (JP)

(72) Inventor: Toshihiko Kaku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 554 days.

(21) Appl. No.: 15/690,294

(22) Filed: Aug. 30, 2017

(65) Prior Publication Data

US 2017/0363857 A1    Dec. 21, 2017

Related U.S. Application Data

(63) Continuation of application No. PCT/JP2016/055559, filed on Feb. 25, 2016.

(30) Foreign Application Priority Data

Mar. 30, 2015 (JP) .................... 2015-070215

(51) Int. Cl.
*A61B 1/04* (2006.01)
*G02B 23/24* (2006.01)
(Continued)

(52) U.S. Cl.
CPC ...... *G02B 23/2476* (2013.01); *A61B 1/00009* (2013.01); *A61B 1/00089* (2013.01);
(Continued)

(58) Field of Classification Search
CPC ... A61B 1/04; A61B 1/00009; A61B 1/00089; A61B 1/00101; A61B 1/00096;
(Continued)

(56) References Cited

U.S. PATENT DOCUMENTS 9,629,647 B2 *   4/2017   Smith ............ A61B 17/320016
2007/0287886 A1  12/2007  Saadat
(Continued)

FOREIGN PATENT DOCUMENTS

| CN | 201675946 | 12/2010 |
| JP | H10-099265 | 4/1998 |

(Continued)

OTHER PUBLICATIONS

"Search Report of European Counterpart Application", dated Mar. 2, 2018, p. 1-p. 6.
(Continued)

*Primary Examiner* — Matthew J Kasztejna
(74) *Attorney, Agent, or Firm* — JCIPRNET

(57) ABSTRACT

There are provided a lesion part volume measuring method and an endoscopic diagnostic apparatus capable of easily detecting the volume of a lesion part without using a special treatment instrument. This problem is solved by detecting the position of a distal end portion of a scope hood from an image captured by an endoscope to which the scope hood is attached, finding the volume of the internal space of the scope hood, which is formed by the scope hood and the distal end surface of an insertion part, from the position of the distal end portion of the scope hood and the model of the endoscope and/or the model of the scope hood, and injecting water into the scope hood and detecting the volume of a lesion part from the difference between the water injection amount and the volume of the internal space of the scope hood.

13 Claims, 5 Drawing Sheets

(51) Int. Cl.
*A61B 1/12* (2006.01)
*A61B 5/107* (2006.01)
*A61B 1/00* (2006.01)
*A61B 1/06* (2006.01)

(52) U.S. Cl.
CPC ............... *A61B 1/04* (2013.01); *A61B 1/12* (2013.01); *A61B 5/1076* (2013.01); *A61B 5/1079* (2013.01); A61B 1/00101 (2013.01); A61B 1/0638 (2013.01); A61B 1/0653 (2013.01); G06T 2207/10068 (2013.01); G06T 2207/30096 (2013.01)

(58) Field of Classification Search
CPC ............ A61B 1/00091; A61B 1/00094; A61B 5/1073; A61B 5/1075
See application file for complete search history.

(56) References Cited

U.S. PATENT DOCUMENTS

| | | | | |
|---|---|---|---|---|
| 2008/0009747 | A1* | 1/2008 | Saadat | A61B 1/04 600/471 |
| 2008/0058591 | A1* | 3/2008 | Saadat | A61B 1/018 600/109 |
| 2009/0203962 | A1 | 8/2009 | Miller et al. | |
| 2013/0096465 | A1* | 4/2013 | Conney | A61B 5/1075 600/587 |
| 2013/0165959 | A1* | 6/2013 | Smith | A61B 17/30 606/170 |
| 2015/0196202 | A1* | 7/2015 | Mercader | A61B 5/0071 600/478 |
| 2017/0251932 | A1* | 9/2017 | Kaku | G06T 1/0007 |
| 2019/0374155 | A1* | 12/2019 | Wang | A61B 1/2736 |

FOREIGN PATENT DOCUMENTS

| | | |
|---|---|---|
| JP | 2001-258822 | 9/2001 |
| JP | 2008-245838 | 10/2008 |
| JP | 2009-531081 | 9/2009 |
| JP | 2011-183000 | 9/2011 |
| JP | 2013-248353 | 12/2013 |

OTHER PUBLICATIONS

"International Search Report (Form PCT/ISA/210) of PCT/JP2016/055559", with English translation thereof, dated May 17, 2016, pp. 1-4.

"Written Opinion (Form PCT/ISA/237) of PCT/JP2016/055559", dated May 17, 2016, with English translation thereof, pp. 1-7.

* cited by examiner

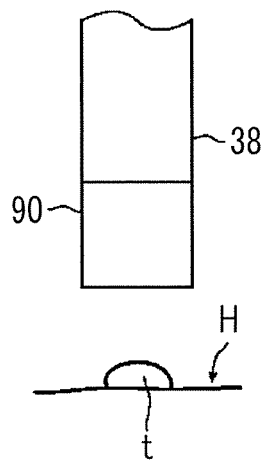 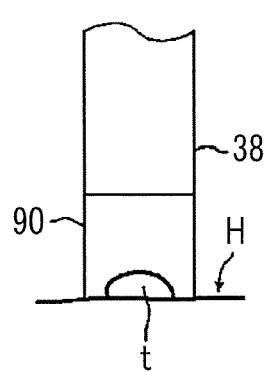 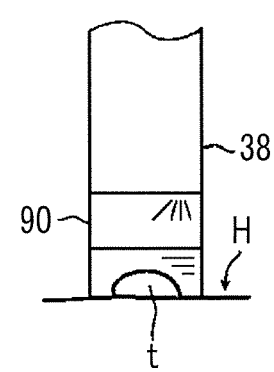 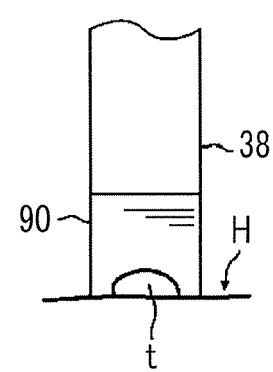
FIG. 6A   FIG. 6B   FIG. 6C   FIG. 6D
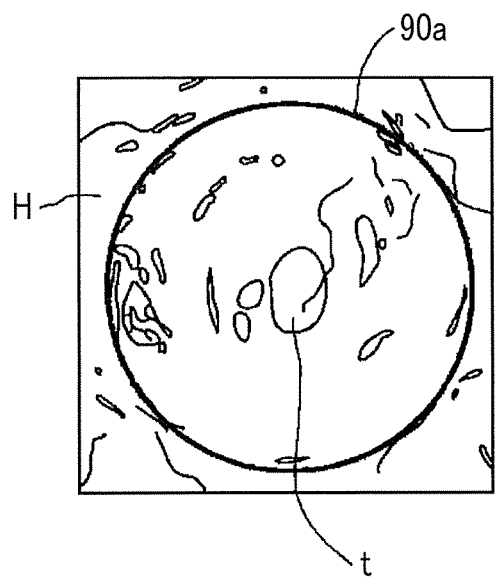
FIG. 7

ENDOSCOPIC DIAGNOSTIC APPARATUS AND LESION PART VOLUME MEASURING METHOD

CROSS-REFERENCE TO RELATED APPLICATIONS

This application is a Continuation of PCT International Application No. PCT/JP2016/ 055559 filed on Feb. 25, 2016, which claims priority under 35 U.S.C § 119(a) to Japanese Patent Application No. 2015-070215 filed on Mar. 30, 2015. Each of the above application(s) is hereby expressly incorporated by reference, in its entirety, into the present application.

BACKGROUND OF THE INVENTION

1. Field of the Invention

The present invention relates to lesion part volume measurement using an endoscope. More specifically, the present invention relates to an endoscopic diagnostic apparatus and a lesion part volume measuring method capable of easily measuring the volume of a lesion part using an endoscope without using a special treatment instrument for measurement.

2. Description of the Related Art

An endoscopic diagnostic apparatus is used to observe the inside of a subject. In the case of observing the inside of the subject, an insertion part of an endoscope is inserted into the body cavity of the subject, for example, white light as observation light is emitted from the distal end portion to a region to be observed, and the reflected light is received, thereby an endoscopic image is captured. The captured endoscopic image is displayed on a display unit, so that the operator of the endoscopic diagnostic apparatus observes the endoscopic image.

In recent years, in addition to checking the presence or absence of a lesion part, such as a tumor, by observing an endoscopic image captured inside the subject, there is a demand to measure the size of a lesion part for the purpose, such as excising a tumor exceeding a certain size and preserving a tumor equal to or less than the certain size to see the state.

In order to measure the size of a lesion part, a method using a treatment instrument, such as a scaled probe, is known. In this method, the scaled probe is inserted from the entrance of the forceps port of the endoscope and is projected from the outlet of the forceps port of the distal end portion. The distal end portion of the scaled probe has flexibility, and is marked with a scale for measuring the size. By pressing such a flexible distal end portion against a region to be observed so that the distal end portion bends and reading the scale marked on the distal end portion, the size of a lesion part in the region to be observed is measured.

In this method, however, it is necessary to insert the scaled probe into the forceps port of the endoscope only in order to measure the size of a lesion part. Not only does the operation require time, but also the operation is complicated and troublesome. Since measurement is performed by pressing the distal end portion of the scaled probe against the region to be observed of the subject so that the distal end portion bends, the measurement accuracy is low, and there are cases in which it is difficult to perform measurement depending on the part, such as a case in which it is difficult to press the distal end portion against the region to be observed of the subject.

Various methods for measuring the size of a lesion part using an endoscope have been proposed.

For example, JP2011-183000A discloses that water flows are injected from two openings of the distal end portion of an insertion part of an endoscope to a lesion part and whether or not the lesion part is equal to or greater than a treatment reference value is determined according to whether or not the distance between the two water flows is equal to the distance between the two openings.

JP2008-245838A discloses that a plurality of measurement points are set around a lesion part using a treatment instrument having an arm portion for setting measurement points and the size of the lesion part is obtained by computation based on the coordinate information of the measurement points.

SUMMARY OF THE INVENTION

In the endoscope apparatus disclosed in JP2011-183000A, a dedicated endoscope having two openings for outputting two water flows from the distal end portion of the insertion part is required. Unless such an endoscope is used, there is a problem that size of a lesion part cannot be measured.

In the endoscope apparatus disclosed in JP2008-245838A, in order to measure the size of a lesion part, a robot arm is required. In addition, there is a problem that a plurality of measurement points should be set around the lesion part by operating the complicated robot arm.

In order to solve the problem of the related art, it is an object of the present invention to provide an endoscopic diagnostic apparatus and a lesion part volume measuring method capable of measuring the volume of a lesion part, such as a tumor, using an endoscope without using a special treatment instrument for measurement.

In order to achieve the aforementioned object, according to an aspect of the present invention, there is provided an endoscopic diagnostic apparatus comprising: an endoscope having a function of injecting water from a distal end of an insertion part; water injection amount detection unit for detecting an amount of water injected from the distal end of the insertion part; a scope hood attached to the distal end of the insertion part of the endoscope; position detection unit for detecting, from an image captured by the endoscope, a position of a distal end portion of the scope hood on the image; model detection unit for detecting at least one of a model of the endoscope or a model of the scope hood; space volume detection unit for detecting a volume of an internal space of the scope hood, which is formed by a distal end surface of the insertion part of the endoscope and the scope hood, using the position of the distal end portion of the scope hood detected by the position detection unit and at least one of the model of the endoscope or the model of the scope hood detected by the model detection unit; and lesion part volume detection unit for detecting a volume of a lesion part from the water injection amount detected by the water injection amount detection unit and the volume of the internal space of the scope hood detected by the space volume detection unit.

In the endoscopic diagnostic apparatus according to the aspect of the present invention, it is preferable that the space volume detection unit detects the volume of the internal space of the scope hood using a relationship between the distal end portion of the scope hood on the image and the volume of the internal space of the scope hood, which is generated according to the model of the scope hood.

In the endoscopic diagnostic apparatus according to the aspect of the present invention, it is preferable that the space volume detection unit detects a distance from the distal end surface of the insertion part of the endoscope to the distal end portion of the scope hood from a position of the distal end portion of the scope hood and detects an area of the distal end surface of the insertion part of the endoscope or an area of a distal end surface of the scope hood from at least one of the model of the endoscope or the model of the scope hood and that the space volume detection unit detects the volume of the internal space of the scope hood using the detected distance from the distal end surface of the insertion part of the endoscope to the distal end portion of the scope hood and the detected area of the distal end surface of the insertion part of the endoscope or the detected area of the distal end surface of the scope hood.

In the endoscopic diagnostic apparatus according to the aspect of the present invention, it is preferable that the space volume detection unit changes a parameter used to detect the volume of the internal space of the scope hood according to at least one of the model of the endoscope or the model of the scope hood.

In the endoscopic diagnostic apparatus according to the aspect of the present invention, it is preferable to further comprise any one or more of flow rate measuring unit for measuring a flow rate of water injected by the endoscope, a tank in which water injected by the endoscope is stored, weight measuring unit for measuring a weight of the tank, time measuring unit for measuring a water injection time by the endoscope, and input unit for inputting a water injection amount. It is preferable that the water injection amount detection unit detects the amount of water injected from the distal end of the insertion part of the endoscope using at least one of a water flow rate measurement result of the flow rate measuring unit, a weight measurement result of the weight measuring unit, a time measurement result of the time measuring unit, and the water injection amount input through the input unit.

In the endoscopic diagnostic apparatus according to the aspect of the present invention, it is preferable to further comprise at least one or more of display unit for displaying the volume of the lesion part detected by the lesion part volume detection unit, recording unit for recording the volume of the lesion part detected by the lesion part volume detection unit, and warning unit for outputting a warning corresponding to the volume of the lesion part detected by the lesion part volume detection unit.

In the endoscopic diagnostic apparatus according to the aspect of the present invention, it is preferable to further comprise water injection amount warning unit for outputting a warning in a case where the water injection amount detected by the water injection amount detection unit exceeds the volume of the internal space of the scope hood detected by the space volume detection unit.

According to another aspect of the present invention, there is provided a lesion part volume measuring method comprising: detecting, from an image captured by an endoscope having a distal end of an insertion part to which a scope hood is attached, a position of a distal end portion of the scope hood on the image; obtaining a volume of an internal space of the scope hood, which is formed by the scope hood and a distal end surface of the insertion part of the endoscope, from the position of the distal end portion of the scope hood on the image and at least one of a model of the endoscope or a model of the scope hood; and injecting water until an inside of the scope hood is filled and measuring a volume of a lesion part from a difference between a water injection amount and the volume of the internal space of the scope hood.

In the lesion part volume measuring method according to the aspect of the present invention, it is preferable that the volume of the internal space of the scope hood is obtained using a relationship between the distal end portion of the scope hood on the image and the volume of the internal space of the scope hood, which is generated according to the model of the scope hood.

In the lesion part volume measuring method according to the aspect of the present invention, it is preferable that a distance from the distal end surface of the endoscope to the distal end portion of the scope hood is detected from a position of the distal end portion of the scope hood on the image, an area of the distal end surface of the endoscope or an area of a distal end surface of the scope hood is detected from at least one of the model of the endoscope or the model of the scope hood, and the volume of the internal space of the scope hood is obtained using the distance from the distal end surface of the endoscope to the distal end portion of the scope hood and the area of the distal end surface of the endoscope or the area of the distal end surface of the scope hood.

In the lesion part volume measuring method according to the aspect of the present invention, it is preferable that a parameter used to obtain the volume of the internal space of the scope hood is changed according to at least one of the model of the endoscope or the model of the scope hood.

In the lesion part volume measuring method according to the aspect of the present invention, it is preferable that an amount of water injected into the scope hood is detected using any one or more of a water flow rate measuring device attached to the endoscope, a change in weight of a tank in which water injected by the endoscope is stored, a time for injection of water into the scope hood, and input of a water injection amount.

In the lesion part volume measuring method according to the aspect of the present invention, it is preferable that any one or more of display of the measured volume of the lesion part, recording of the measured volume of the lesion part, and output of a warning corresponding to the measured volume of the lesion part are performed.

In the lesion part volume measuring method according to the aspect of the present invention, it is preferable that a warning is output in a case where an amount of water injected into the scope hood becomes larger than the volume of the internal space of the scope hood.

According to the present invention, the volume of a lesion part, such as a tumor, can be easily measured using a scope hood, which is generally used as a treatment instrument of an endoscope, and a water injection function that the endoscope generally has, without using a special treatment instrument.

BRIEF DESCRIPTION OF THE DRAWINGS

FIGS. 6A to 6D are conceptual diagrams illustrating the operation of the present invention.

FIG. 7 is a conceptual diagram showing an endoscopic image in which a scope hood is imaged.

DESCRIPTION OF THE PREFERRED EMBODIMENTS

Hereinafter, an endoscopic diagnostic apparatus and a lesion part volume measuring method of the present invention will be described in detail based on preferred embodiments shown in accompanying diagrams.

Figure 1:
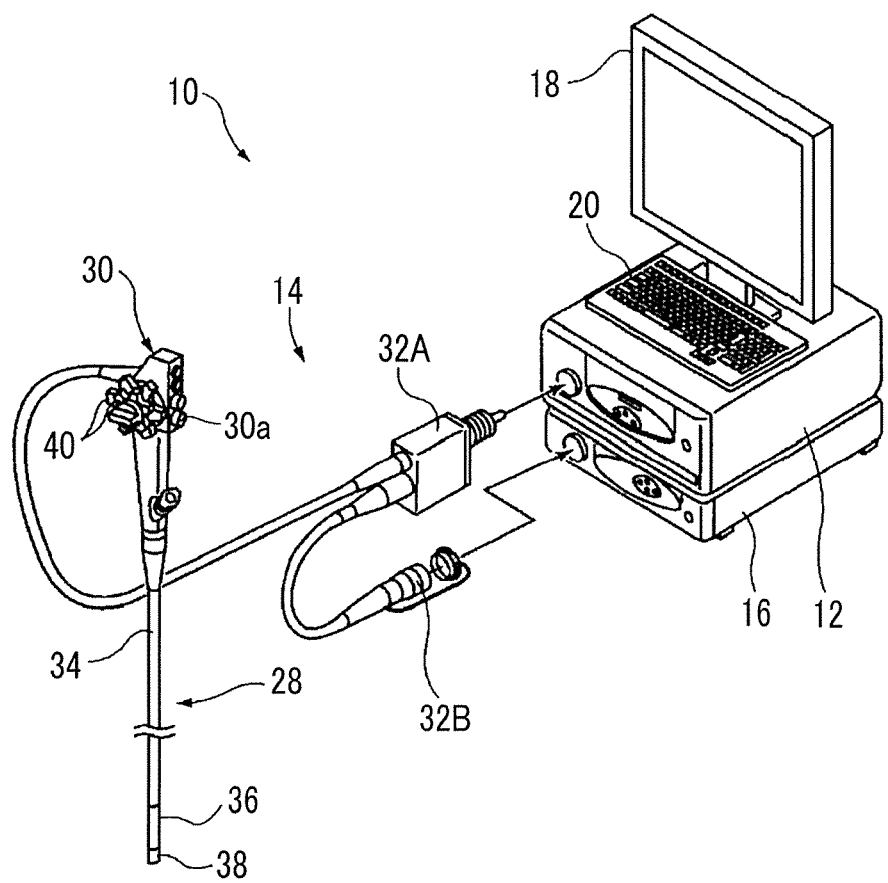
FIG. 1 is a conceptual diagram showing an example of an endoscopic diagnostic apparatus of the present invention.
Figure 2:
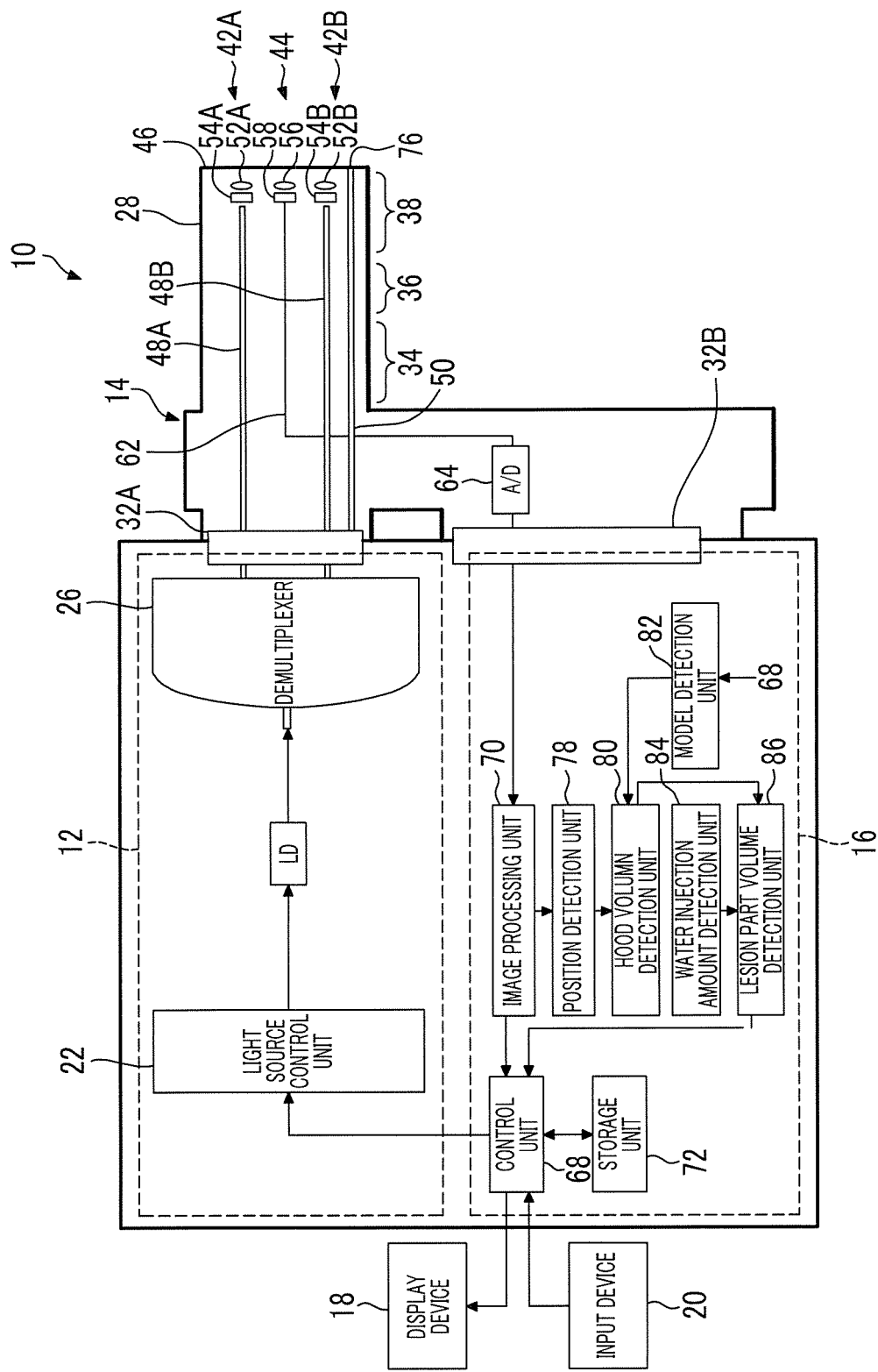
FIG. 2 is a block diagram showing the internal configuration of the endoscopic diagnostic apparatus shown in FIG. 1.

FIG. 1 conceptually shows an example of an endoscope apparatus of the present invention for carrying out the lesion part volume measuring method of the present invention. FIG. 2 is a block diagram showing the internal configuration of the endoscopic diagnostic apparatus shown in FIG. 1.

As shown in FIGS. 1 and 2, an endoscopic diagnostic apparatus 10 is configured to include a light source device 12, an endoscope 14 for capturing an endoscopic image of a region to be observed of a subject with observation light supplied from the light source device 12, a processor device 16 for performing image processing on the endoscopic image captured by the endoscope 14, a display device 18 for displaying an endoscopic image after the image processing that is output from the processor device 16, and an input device 20 for receiving an input operation.

As shown in FIG. 2, the light source device 12 is configured to include a light source control unit 22, a laser light source LD, and an optical splitter 26.

In the light source device 12 in the shown example, narrowband light having a center wavelength of 445 nm and a certain wavelength range (for example, center wavelength±10 nm) of blue is emitted from the laser light source LD. The laser light source LD is a light source that emits excitation light for generating white light (pseudo-white light) from a phosphor, which will be described later, as illumination light, and ON/OFF (turn on/turn off) control and light amount control are performed by the light source control unit 22 controlled by a control unit 68 of the processor device 16 to be described later.

As the laser light source LD, a broad area type InGaN-based laser diode can be used, and an InGaNAs-based laser diode or a GaNAs-based laser diode can also be used.

The white light source for generating the white light is not limited to the combination of the excitation light and the phosphor, but any thing that emits white light may be used. For example, a xenon lamp, a halogen lamp, and a white LED (light emitting diode) can be used. The wavelength of laser light emitted from the laser light source LD is not limited to the above example, but laser light having a wavelength that plays a similar role can be appropriately selected.

The laser light emitted from the laser light source LD is incident on the optical fiber through a condensing lens (not shown), and is transmitted to a connector unit 32A after being demultiplexed into two systems of light by the optical splitter 26. The optical splitter 26 is a half mirror, a reflecting mirror, or the like.

The endoscope 14 is an electronic endoscope having an illumination optical system, which emits two systems (two lamps) of illumination light from the distal end surface of an insertion part inserted into the subject, and an imaging optical system of one system (one eye) for capturing an endoscopic image of a region to be observed.

The endoscope 14 includes an insertion part 28, an operation unit 30 for performing an operation for bending the distal end of the insertion part 28 or an operation for observation, the connector unit 32A for detachably connecting the endoscope 14 and the light source device to each other, and a connector unit 32B for detachably connecting the endoscope 14 and the processor device 16 to each other.

A water supply connector for connecting the endoscope 14 and a water supply source to each other and an air supply connector for connecting the endoscope 14 and an air supply source to each other are provided on the back surface side of the connector unit 32A in FIG. 1.

Basically, the endoscope 14 is a known electronic endoscope except lesion part volume measurement to be described later.

The insertion part 28 is configured to include a soft portion 34 having flexibility, a bending portion 36, and an endoscope distal end portion 38.

The bending portion 36 is provided between the soft portion 34 and the endoscope distal end portion 38, and is configured to be freely bent by the rotating operation of an angle knob 40 disposed in the operation unit 30. The bending portion 36 can be bent in an arbitrary direction and at an arbitrary angle according to a part of the subject or the like for which the endoscope 14 is used. Accordingly, the endoscope distal end portion 38 can be directed to a desired observation part.

Figure 3:
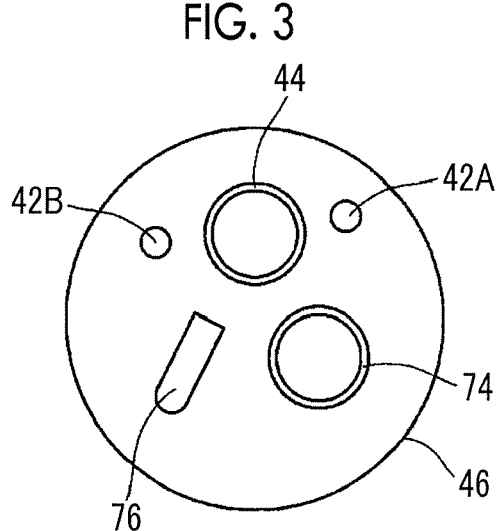
FIG. 3 is a conceptual diagram showing the configuration of a distal end portion of an endoscope.

As shown in FIG. 3, two illumination windows 42A and 42B through which light is emitted to a region to be observed, one observation window 44 for capturing reflected light from the region to be observed, a forceps port 74 serving as an outlet of a treatment instrument, such as a forceps inserted into a forceps channel provided inside the insertion part 28, an air and water supply port 76 serving as an outlet of an air and water supply channel 50, and the like are disposed on an endoscope distal end surface 46 that is the distal end surface of the insertion part 28 (endoscope distal end portion 38).

The observation window 44, the forceps port 74, and the air and water supply port 76 are disposed in a central portion of the endoscope distal end surface 46. The illumination windows 42A and 42B are disposed on both sides of the observation window 44.

The air and water supply port 76 is for cleaning the observation window 44 by spraying water and air. The air and water supply port 76 is connected to the air and water supply channel 50. The air and water supply channel 50 is connected to the water supply connector and the air supply connector of the connector unit 32A through the endoscope distal end portion 38, the bending portion 36, and the soft portion 34 of the insertion part 28 and the operation unit 30 (air and water supply button 30a) from the air and water supply port 76.

Similarly to a normal endoscope, in the endoscope 14, air and water can be supplied through the air and water supply port 76 on the endoscope distal end surface 46 of the insertion part 28 by operating the air and water supply button 30a of the operation unit 30.

In the endoscope 14 in the shown example, air supply and water supply are for cleaning the observation window 44. However, the present invention is not limited thereto. That is, in the endoscope apparatus of the present invention, air supply and water supply may be for cleaning the region to be observed. Alternatively, the endoscope apparatus of the present invention may have both a function of supplying air and water for cleaning the observation window 44 and a function of supplying air and water for cleaning the region to be observed.

An optical fiber 48A is housed behind the illumination window 42A. The optical fiber 48A is placed in the light source device 12 through the endoscope distal end portion 38, the bending portion 36, and the soft portion 34 of the insertion part 28 and the connector unit 32A. A phosphor 54A is disposed before the distal end portion (illumination window 42A side) of the optical fiber 48A, and an optical system, such as a lens 52A, is attached before the phosphor 54A. Similarly, behind the illumination window 42B, an optical fiber 48B having an optical system, such as a phosphor 54B and a lens 52B, in its distal end portion is housed.

The phosphors 54A and MB contain a plurality of kinds of fluorescent materials (for example, a YAG-based fluorescent material or a fluorescent material, such as BAM (BaMgAl$_{10}$O$_{17}$)) that are excited to emit light of green to yellow by absorbing some of blue laser light beams from the laser light source LD. When excitation light for white light observation is emitted to the phosphors 54A and 54B, excited emission light (fluorescence) of green to yellow emitted from the phosphors 54A and 54B and blue laser light, which is transmitted through the phosphors 54A and 54B without being absorbed by the phosphors 54A and 54B, are combined with each other. As a result, white light (pseudo-white light) is generated.

Figure 4:
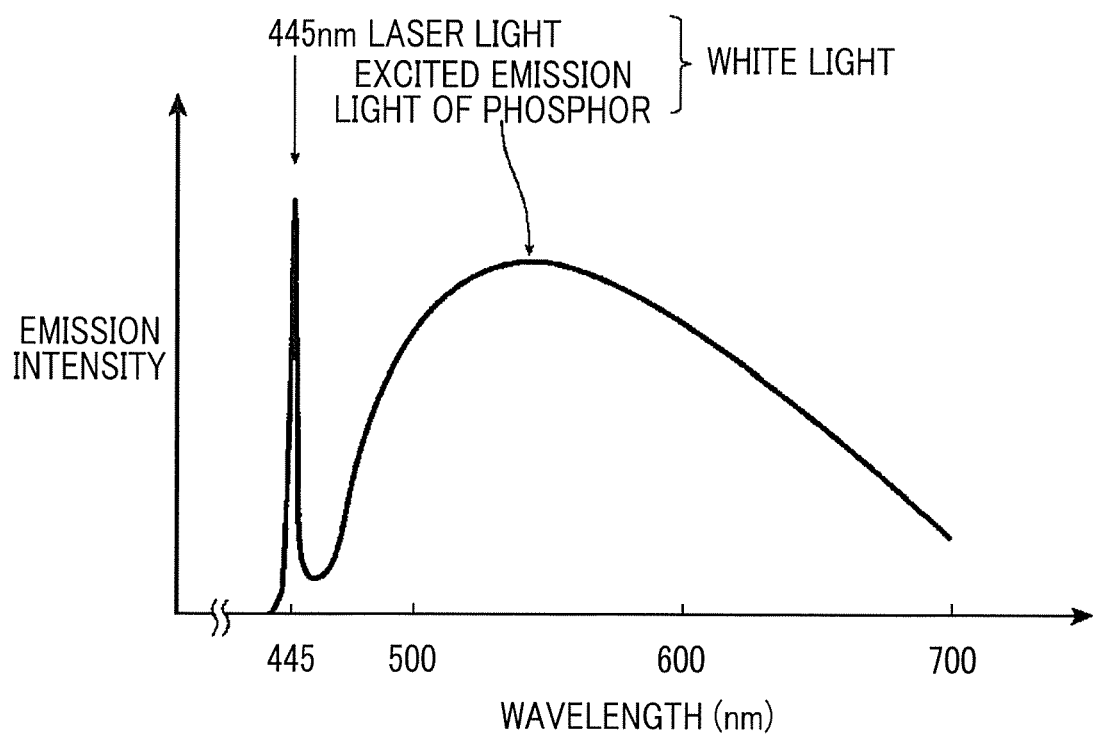
FIG. 4 is a graph showing blue laser light from a blue laser light source and an emission spectrum obtained by wavelength-converting the blue laser light using a phosphor.

FIG. 4 is a graph showing blue laser light from a blue laser light source and an emission spectrum obtained by wavelength-converting the blue laser light using a phosphor. The blue laser light emitted from the laser light source LD is expressed by a bright line with a center wavelength of 445 nm, and the excited emission light from the phosphors 54A and 54B due to the blue laser light has a spectral intensity distribution in which the emission intensity increases in the wavelength range of approximately 450 nm to 700 nm. The above-described pseudo-white light is formed by the combined light of the excited emission light and the blue laser light.

Here, the white light referred to in the present invention is not limited to strictly including all wavelength components of visible light. For example, the white light referred to in the present invention may include light in a specific wavelength band, such as R (red), G (green), and B (blue) that are reference colors, including the above-described pseudo-white light. That is, the white light referred to in the present invention broadly includes light including wavelength components ranging from green to red or light including wavelength components from blue to green, for example.

The illumination optical system on the illumination window 42A side and the illumination optical system on the illumination window 42B side have the same configuration and function. From the illumination windows 42A and 42B, basically the same illumination light is emitted at the same time. Different illumination light beams can be emitted through the illumination windows 42A and 42B. It is not essential to have an illumination optical system that emits two systems of illumination light. For example, the same function can also be realized in an illumination optical system that emits one system of illumination light or four systems of illumination light.

An optical system, such as an objective lens unit 56 for capturing image light of the region to be observed of the subject, is attached behind the observation window 44. In addition, an imaging device 58, such as a charge coupled device (CCD) image sensor or a complementary metal-oxide semiconductor (CMOS) image sensor for acquiring the image information of the region to be observed, is attached behind the objective lens unit 56.

The imaging device 58 receives light from the objective lens unit 56 on the imaging surface (light receiving surface), performs photoelectric conversion of the received light, and outputs an imaging signal (analog signal). On the imaging surface of the imaging device 58, color filters of R color (about 580 nm to 760 nm), G color (about 450 nm to 630 nm), and B color (about 380 nm to 510 nm) having spectral transmittances for dividing the wavelength range of about 370 to 720 nm of visible light into three parts are provided. With pixels of three colors of an R pixel, a G pixel, and a B pixel as a set, a plurality of sets of pixels are arranged in a matrix.

The light guided by the optical fibers 48A and 48B from the light source device 12 is emitted from the endoscope distal end portion 38 toward the region to be observed of the subject. Then, the state of the region to be observed, to which the illumination light is emitted, is formed on the imaging surface of the imaging device 58 by the objective lens unit 56 and is photoelectrically converted by the imaging device 58, so that imaging is realized. From the imaging device 58, an imaging signal (analog signal) of the capture endoscopic image of the region to be observed of the subject is output.

The imaging signal (analog signal) of the endoscopic image output from the imaging device 58 is input to an A/D converter 64 through a scope cable 62. The A/D converter 64 converts the imaging signal (analog signal) from the imaging device 58 into an image signal (digital signal). The converted image signal is input to an image processing unit 70 of the processor device 16 through the connector unit 32B.

The processor device 16 includes the control unit 68, the image processing unit 70, a storage unit 72, a position detection unit 78 (corresponding to position detection unit), a hood volume detection unit 80, a model detection unit 82 (corresponding to a model detection unit), a water injection amount detection unit 84 (corresponding to water injection amount detection unit), and a lesion part volume detection unit 86 (corresponding to lesion part volume detection unit). The display device 18 and the input device 20 are connected to the control unit 68. The processor device 16 controls the light source control unit 22 of the light source device 12 based on an instruction input through the imaging switch of the endoscope 14 or the input device 20, performs image processing on the image signal of the endoscopic image input from the endoscope 14, and outputs an endoscopic image after the image processing to the display device 18. The processor device 16 may be configured by using a computer, for example.

The image processing unit 70 performs various kinds of predetermined image processing on the image signal of the endoscopic image input from the endoscope 14, and outputs an image signal of the endoscopic image after the image processing. The image signal of the endoscopic image after the image processing is transmitted to the control unit 68.

In the case of measuring the volume of a lesion part as will be described later, the image signal of the endoscopic image after the image processing generated by the image processing unit 70 is also supplied to the position detection unit 78.

The position detection unit 78 detects the position of the distal end portion of a scope hood 90, which is attached to the endoscope distal end portion 38 of the endoscope 14, from the endoscopic image.

Figure 5A:
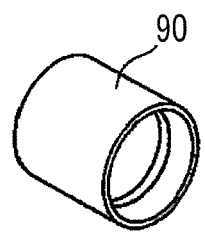
FIG. 5A is a conceptual diagram showing the configuration of a scope hood attached to a distal end portion of an insertion part of an endoscope.
Figure 5B:
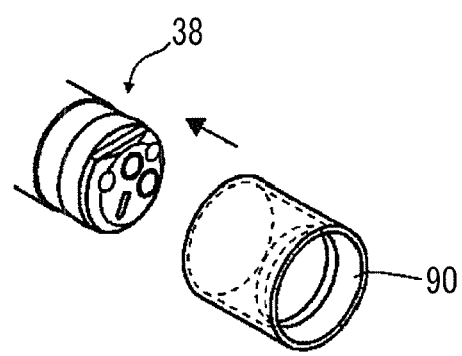
FIG. 5B is a conceptual diagram showing how the scope hood shown in FIG. 5A is attached to the distal end portion of the insertion part of the endoscope.

FIG. 5A is a conceptual diagram of an example of the scope hood 90 (hereinafter, also referred to as a hood 90), and FIG. 5B is a conceptual diagram showing how the hood 90 is attached to the endoscope distal end portion 38.

The hood 90 is a cylindrical object that can be detachably attached to the endoscope distal end portion 38, and is used to ensure a field of view, ensure an appropriate imaging distance with respect to a portion to be observed, assist treatment with various treatment instruments, and the like.

As such a hood 90, various models corresponding to the model of the endoscope 14 are prepared for each model of the endoscope 14. In the present invention, any known hood 90 can be used as long as the hood corresponds to the model of the endoscope 14. Accordingly, the hood 90 may have a straight tube shape, or may have a shape whose diameter gradually decreases from the middle toward the distal end.

The position detection unit 78 detects, from the endoscopic image captured by the endoscope 14 with the hood 90 attached thereto and processed by the image processing unit 70, the position of the distal end portion (end portion on a side opposite to the insertion part 28) of the hood 90 on the endoscopic image.

The model detection unit 82 detects the model of the endoscope 14 and/or the model of the hood 90 attached to the endoscope distal end portion 38.

The hood volume detection unit 80 detects the volume of the internal space of the hood 90, which is formed by the distal end surface of the endoscope 14 and the hood 90, using the distal end position of the hood 90 detected by the position detection unit 78 and the model of the endoscope 14 and/or the model of the hood 90 detected by the model detection unit 82.

At the time of observation with the endoscope 14 using the hood 90, the distal end of the hood 90 is usually brought into close contact with the region to be observed of the subject. That is, in other words, the hood volume detection unit 80 detects the volume of the space, which is formed by the distal end surface of the endoscope 14, the inner surface of the hood 90, and the surface of the subject, that is, the open face on the distal end side of the hood 90, corresponding to a state in which the distal end of the hood 90 is brought into close contact with the region to be observed of the subject.

The water injection amount detection unit 84 detects the amount of water injected into the hood 90 in the case of measuring the volume of a lesion part as will be described later.

As described above, in the endoscope 14, water for cleaning the observation window 44 can be sprayed from the air and water supply port 76 by operating the air and water supply button 30a. In the endoscopic diagnostic apparatus 10 of the present invention, using this, water is injected into the hood 90 attached to the endoscope distal end portion 38 in the case of measuring the volume of a lesion part as will be described later. At this time, the water injection amount detection unit 84 detects the amount of water injected into the hood 90.

The lesion part volume detection unit 86 detects the volume of a lesion part, such as a tumor, from the difference between the volume of the internal space of the hood 90 detected by the hood volume detection unit 80 and the amount of water injected into the hood 90 detected by the water injection amount detection unit 84.

The position detection unit 78, the hood volume detection unit 80, the model detection unit 82, the water injection amount detection unit 84, and the lesion part volume detection unit 86 will be described in detail later.

The control unit 68 performs overall control of the endoscopic diagnostic apparatus 10, such as the display of the display device 18, the operation of the light source control unit 22, and the image processing of the image processing unit 70. Based on an instruction from the imaging switch of the endoscope 14 or the input device 20, the control unit 68 controls the operation of the light source control unit 22 of the light source device 12, or performs control such that an endoscopic image is stored in the storage unit 72 with, for example, one (one frame) endoscopic image as a unit.

The input device 20 is a known input device, such as a keyboard or a mouse. The display device is also a known display device (display), such as a liquid crystal display.

Hereinafter, the endoscopic diagnostic apparatus and the lesion part volume measuring method of the present invention will be described in detail by describing the operation of the endoscopic diagnostic apparatus 10.

First, an operation in the case of capturing an endoscopic image will be described.

At the time of normally capturing an endoscopic image, the laser light source LD is turned on with a fixed light emission amount set in advance under the control of the light source control unit 22. Laser light having a center wavelength of 445 nm emitted from the laser light source LD is emitted to the phosphors 54A and 54B, and white light is emitted from the phosphors 54A and 54B. The white light emitted from the phosphors 54A and 54B is emitted to the subject, and the reflected light is received by the imaging device 58. As a result, an endoscopic image of the region to be observed of the subject is captured.

The imaging signal (analog signal) of the endoscopic image output from the imaging device 58 is converted into an image signal (digital signal) by the A/D converter 64, various kinds of image processing is performed by the image processing unit 70, and an image signal of the endoscopic image after the image processing is output. Then, an endoscopic image corresponding to the image signal of the endoscopic image after the image processing is displayed on the display device 18 by the control unit 68. If necessary, the image signal of the endoscopic image is stored in the storage unit 72.

The endoscopic diagnostic apparatus 10 of the present invention has a function of detecting the volume of a lesion part, such as a tumor, in a region to be observed. Therefore, the volume of a lesion part is detected, for example, by selection of a mode such as a volume measurement mode or by an instruction using a switch, such as a volume measurement switch.

In the present invention, the volume of a lesion part is detected using the hood 90 attached to the endoscope distal end portion 38 of the insertion part 28 as described above.

In the case of detecting the volume of a lesion part, an operator of the endoscope, such as a doctor, attaches the hood 90 to the endoscope distal end portion 38, inserts the insertion part 28 into the body cavity, and operates the endoscope 14 so that the endoscope distal end portion 38 is brought close to a target region to be observed, such as a place where a lesion part t such as a tumor of a subject H is present, as conceptually shown in FIG. 6A. In the meantime, as described above, an endoscopic image of the region to be observed of the subject is captured and displayed on the display device 18.

The endoscope distal end portion 38 is brought closer to the target region to be observed, so that the distal end of the hood 90 is brought into close contact with the region to be observed of the subject H as conceptually shown in FIG. 6B. As a result, the observation field of view and the imaging distance in the endoscope 14 are secured by the operation of the hood 90.

In this state, for example, in a case where the volume measurement mode is selected, the endoscopic image is supplied to the position detection unit 78.

The model detection unit 82 detects the model of the endoscope 14 and/or the model of the attached hood 90, and transmits the detected information to the hood volume detection unit 80 (corresponding to space volume detection unit). In the endoscopic diagnostic apparatus 10, usually, the information of the endoscope 14 is supplied from the endoscope 14 to the control unit 68 of the processor device 16 when the connector unit 32A is connected to the processor device 16. The model detection unit 82 may detect the model of the endoscope 14 using the information. For the model of the hood 90, for example, it is preferable that input unit, with which the user inputs the model of the hood 90 by a graphical user interface (GUI) using the input device 20 and the display device 18, is provided and the model detection unit 82 detects the model of the hood 90 using the information input through the input unit. The model of the endoscope 14 may be input using the same method.

The position detection unit 78 detects the position of the distal end portion of the hood 90 on the endoscopic image from the capture endoscopic image.

FIG. 7 conceptually shows an endoscopic image captured in a state in which the hood 90 is attached to the endoscope distal end portion 38. In the endoscopic image captured in a state in which the hood 90 is attached, the hood 90 is imaged. The position detection unit 78 detects a hood distal end portion 90a, which is a distal end portion of the hood 90, on the image from the endoscopic image. The hood distal end portion 90a may be detected using a known method, such as edge detection or circle fitting (pattern matching).

The position detected result of the hood distal end portion 90a detected by the position detection unit 78 is supplied to the hood volume detection unit 80.

The hood volume detection unit 80 detects the volume of the internal space of the hood 90, which is formed by the distal end surface of the endoscope 14 and the hood 90, using the information of the position of the hood distal end portion 90a on the endoscopic image supplied from the position detection unit 78 and the information of the model of the endoscope 14 and/or the model of the attached hood 90 supplied from the model detection unit 82.

As is well known, the operator of the endoscope 14, such as a doctor, attaches the hood 90 by fitting the hood 90 so that the endoscope distal end portion 38 of the insertion part 28 is fitted.

The pressing amount of the hood 90 at this time is not necessarily constant. That is, the volume of the internal space of the hood 90 changes depending on the pressing amount of the hood 90 by the operator.

Here, in the case of the same hood 90, the position of the inner periphery of the hood distal end portion 90a, the inner peripheral length, the diameter, and the like on the endoscopic image are uniquely determined according to the pressing amount of the hood 90. That is, in a case where the pressing amount is large, the distance between the endoscope distal end surface 46 and the hood distal end portion 90a decreases. Accordingly, since the inner periphery of the hood distal end portion 90a is shifted to the outside on the image, the inner periphery length or the diameter increases. Conversely, in a case where the pressing amount is small, the distance between the endoscope distal end surface 46 and the hood distal end portion 90a increases. Accordingly, since the inner periphery of the hood distal end portion 90a is shifted to the inside on the image, the inner periphery length or the diameter decreases.

Accordingly, if the model of the hood 90 is known, the pressing amount of the hood 90 can be known by the position of the inner periphery of the hood distal end portion 90a, the inner peripheral length, the diameter, and the like on the endoscopic image. If the model of the hood 90 is the same, the volume of the internal space of the hood 90 with respect to the pressing amount is uniquely determined.

Corresponding to this, in the endoscopic diagnostic apparatus 10, for example, a lookup table (LUT) showing the relationship between the inner peripheral length of the hood distal end portion 90a on the endoscopic image and the volume of the internal space of the hood 90 is generated for each model of the hood 90, and is stored in the hood volume detection unit 80. The hood volume detection unit 80 selects a corresponding LUT according to the information of the model of the hood 90, and detects the inner peripheral length of the hood distal end portion 90a on the endoscopic image from the position of the distal end portion on the endoscopic image and detects the volume of the internal space of the hood 90 from the inner peripheral length using selected LUT.

Instead of the inner peripheral length of the hood distal end portion 90a, the position, diameter, radius, and the like of the inner periphery of the hood distal end portion 90a on the endoscopic image can also be used.

In addition to this, various methods can be used for detection of the volume of the internal space of the hood 90.

For example, if the model of the endoscope 14 is known, the area, the inner peripheral length, the diameter, and the like of the endoscope distal end surface 46 of the endoscope 14 can be known. In a case where the hood 90 has a straight tube shape, the endoscope distal end surface 46 of the endoscope 14 and the hood distal end portion 90a have the same size and shape.

That is, in a case where the hood 90 has a straight tube shape, if the model of the endoscope 14 is known, the pressing amount of the hood 90 can be similarly known by the position of the inner periphery of the hood distal end portion 90a, the inner peripheral length, the diameter, and the like on the endoscopic image.

Therefore, similarly, an LUT showing the relationship between the inner peripheral length of the hood distal end portion 90a on the endoscopic image and the volume of the internal space of the hood 90 may be generated in advance for each model of the endoscope 14, a corresponding LUT may be selected according to the information of the model of the endoscope 14, the inner peripheral length of the hood distal end portion 90a may be detected from the position of the distal end portion on the endoscopic image, and the volume of the internal space of the hood 90 may be detected from the inner peripheral length using the selected LUT.

In the endoscopic diagnostic apparatus 10, in addition to the above-described method, the volume of the internal space of the hood 90 may be detected by calculation. As described above in the case of the same hood 90, the position of the inner periphery of the hood distal end portion 90a, the inner peripheral length, the diameter, and the like on the endoscopic image are uniquely determined according to the pressing amount of the hood 90. That is, the position of the inner periphery of the hood distal end portion 90a, the inner peripheral length, the diameter, and the like on the endoscopic image uniquely correspond to a distance between the endoscope distal end surface 46 of the insertion part 28 of the endoscope 14 and the distal end portion of the hood 90 (hereinafter, the distance is also simply referred to as a "hood length").

If the model of the hood 90 is known, the area of the hood distal end portion 90a can be known.

Therefore, the volume of the internal space of the hood 90 may be detected by generating, for example, an LUT showing the relationship between the inner peripheral length of the hood distal end portion 90a on the endoscopic image and the hood length for each model of the hood 90, selecting an LUT according to the model of the hood (equivalent to changing a parameter used to detect the volume of the internal space of the scope hood), detecting the inner peripheral length of the hood distal end portion 90a from the position of the distal end portion on the endoscopic image, detecting the hood length from the inner peripheral length, and integrating the hood length and the area of the hood distal end portion 90a.

This method can be appropriately used in a case where the hood 90 has a straight tube shape.

As described above, in a case where the hood 90 has a straight tube shape, the endoscope distal end surface 46 of the insertion part 28 of the endoscope 14 and the hood distal end portion 90a have the same size and shape. If the model of the endoscope 14 is known, the area of the endoscope distal end surface 46 can be known.

Therefore, similarly, the volume of the internal space of the hood 90 may be detected by generating, for example, an LUT showing the relationship between the inner peripheral length of the hood distal end portion 90a on the endoscopic image and the hood length for each model of the endoscope 14, selecting an LUT according to the model of the endoscope 14 (equivalent to changing a parameter used to detect the volume of the internal space of the scope hood), detecting the inner peripheral length of the hood distal end portion 90a from the position of the distal end portion on the endoscopic image, detecting the hood length from the inner peripheral length, and integrating the hood length and the area of the hood distal end portion 9a.

The hood volume detection unit 80 supplies the detection result of the volume of the internal space of the hood 90 to the lesion part volume detection unit 86.

A plurality of methods for detecting the volume of the inner space of the hood 90 may be used in combination, and a plurality of detection methods may be set so that the operator can select the detection method.

On the other hand, in a case where the volume measurement mode is selected, the operator operates the air and water supply button 30a to inject water into the hood 90 as shown in FIG. 6C. According to the selection of the volume measurement mode, the start of water injection may be prompted by displaying on the display device 18, sound output, or the like.

As shown in FIG. 6D, if the inside of the hood 90 is filled with water, the water injection is ended.

In a case where the water injection is ended, the water injection amount detection unit 84 detects the amount of water injected into the hood 90, and supplies the detection result of the water injection amount to the lesion part volume detection unit 86.

Various methods can be used for detection of the amount of water injected into the hood 90.

As an example, a method is exemplified in which a flow meter (corresponding to flow rate measuring unit) is provided somewhere in the air and water supply channel of the insertion part 28 and the amount of water injected into the hood 90 is obtained from the flow rate measurement result of the flow meter.

Usually, water injection is performed using a pump or the like having a constant flow rate. Accordingly, it is possible to use a method in which a timer for measuring the water injection time (corresponding to time measuring unit) or the like is provided and the water injection amount is calculated from the flow rate of the pump and the water injection time measured by the timer or the like.

In addition, there is also a case where the endoscopic diagnostic apparatus 10 includes a tank for storing water to be injected. Accordingly, it is also possible to use a method in which a weight meter (corresponding to weight measuring unit) for measuring the weight of a tank before and after water injection or the like is provided and the water injection amount is obtained from the weight measurement result of the weight meter or the like.

For example, it is also possible to use a method in which input unit for inputting the water injection amount is provided by a GUI using the input device 20 and the display device 18 or the like and the water injection amount input through the input unit is used. This method is effectively used in a case where the operator injects water into the hood 90 through a forceps port or the like using a syringe or the like.

A plurality of methods for detecting the water injection amount may be used in combination, and a plurality of detection methods may be set so that the operator can select the detection method.

In a case where the amount of water injected into the hood exceeds the internal volume of the hood 90 detected by the hood volume detection unit 80, a warning may be issued by displaying on the display device 18, sound output, or the like (corresponding to water injection amount warning unit). In addition to the warning, display or sound output prompting to redo the operation of detecting the volume of the lesion part t may be performed.

The lesion part volume detection unit 86 detects the volume of the lesion part t by subtracting the amount of water injected into the hood 90, which is supplied from the water injection amount detection unit 84, from the internal volume of the hood 90 supplied from the hood volume detection unit 80.

If there is no lesion part t, such as a tumor, the internal volume of the hood 90 and the amount of water injected into the hood 90 should be the same. In contrast, in a case where the lesion part t is present in the region to be observed of the subject H, the amount of water that can be injected into the hood 90 is reduced by the volume of the lesion part t. Therefore, the volume of the lesion part t can be detected by subtracting the amount of water injected into the hood 90 from the internal volume of the hood 90.

As described above, according to the present invention, the volume of a lesion part, such as a tumor, can be measured using a hood, which is generally used in the endoscopic diagnostic apparatus, and a water injection function that the endoscope generally has, without using a special treatment instrument for measurement or the like.

The volume of the lesion part t detected by the lesion part volume detection unit 86 is supplied to the control unit 68.

The control unit 68 displays the detection result of the volume of the lesion part t on the display device 18 (corresponding to display unit), and stores (records) the detection result of the volume of the lesion part t in the storage unit 72 (corresponding to recording unit). It is preferable to store the detection result of the volume of the lesion part t so as to be associated with a corresponding endoscopic image, such as an endoscopic image at the time when the volume detection mode is selected, for example.

In a case where the volume of the lesion part t exceeds a predetermined threshold value, a warning may be issued by displaying on the display device 18, sound output, or the like (corresponding to warning unit).

While the endoscopic diagnostic apparatus and the lesion part volume measuring method of the present invention have been described in detail, the present invention is not limited to the examples described above, but various improvements and changes may be made without departing from the scope and spirit of the present invention.

The present invention can be appropriately used for various diagnoses using an endoscope.

EXPLANATION OF REFERENCES

10: endoscopic diagnostic apparatus
12: light source device
14: endoscope
16: processor device
18: display device
20: input device
22: light source control unit
26: optical splitter
28: insertion part
30: operation unit
30a: air and water supply button
32A, 32B: connector unit
34: soft portion
36: bending portion
38: distal end portion
40: angle knob
42A, 42B: illumination window
44: observation window
46: distal end surface
48A, 48B: optical fiber
50: air and water supply channel
52A, 52B: lens
54A, 54B: phosphor
56: objective lens unit
58: imaging device
62: scope cable
64: A/D converter
68: control unit
70: image processing unit
72: storage unit
74: forceps port
76: air and water supply port
78: position detection unit
80: hood volume detection unit
82: model detection unit
84: water injection amount detection unit
86: lesion part volume detection unit
LD: laser light source

What is claimed is:

1. An endoscopic diagnostic apparatus, comprising:
   an endoscope having a function of injecting water from a distal end of an insertion part;
   a scope hood attached to the distal end of the insertion part of the endoscope; and
   a processor configured to:
   detect an amount of water injected from the distal end of the insertion part;
   detect, from an image captured by the endoscope, a position of a distal end portion of the scope hood on the image;
   detect at least one of a model of the endoscope or a model of the scope hood;
   detect a volume of an internal space of the scope hood, which is formed by a distal end surface of the insertion part of the endoscope and the scope hood, using the position of the distal end portion of the scope hood detected by the processor and at least one of the model of the endoscope or the model of the scope hood detected by the processor; and
   detect a volume of a lesion part from the water injection amount detected by the processor and the volume of the internal space of the scope hood detected by the processor.

2. The endoscopic diagnostic apparatus according to claim 1,
   wherein the processor detects the volume of the internal space of the scope hood using a relationship between the distal end portion of the scope hood on the image and the volume of the internal space of the scope hood, which is generated according to the model of the scope hood.

3. The endoscopic diagnostic apparatus according to claim 2, wherein the processor changes a parameter used to detect the volume of the internal space of the scope hood according to at least one of the model of the endoscope or the model of the scope hood.

4. The endoscopic diagnostic apparatus according to claim 2, further comprising:
   any one or more of a flow meter for measuring a flow rate of water injected by the endoscope, a tank in which water injected by the endoscope is stored, a weight meter for measuring a weight of the tank, a timer for measuring a water injection time by the endoscope, and an input device for inputting a water injection amount,
   wherein the processor detects the amount of water injected from the distal end of the insertion part of the endoscope using at least one of a water flow rate measurement result of the flow meter, a weight measurement result of the weight meter, a time measurement result of the timer, and the water injection amount input through the input device.

5. The endoscopic diagnostic apparatus according to claim 2, further comprising:
   any one or more of a display device for displaying the volume of the lesion part detected by the processor or outputting a warning corresponding to the volume of the lesion part detected by the processor, and a memory for recording the volume of the lesion part detected by the processor.

6. The endoscopic diagnostic apparatus according to claim 1,
   wherein the processor detects a distance from the distal end surface of the insertion part of the endoscope to the distal end portion of the scope hood from a position of the distal end portion of the scope hood, and detects an area of the distal end surface of the insertion part of the endoscope or an area of a distal end surface of the scope hood from at least one of the model of the endoscope or the model of the scope hood, and the processor detects the volume of the internal space of the scope hood using the detected distance from the distal end surface of the insertion part of the endoscope to the distal end portion of the scope hood and the detected area of the distal end surface of the insertion part of the endoscope or the detected area of the distal end surface of the scope hood.

7. The endoscopic diagnostic apparatus according to claim 6,
wherein the processor changes a parameter used to detect the volume of the internal space of the scope hood according to at least one of the model of the endoscope or the model of the scope hood.

8. The endoscopic diagnostic apparatus according to claim 6, further comprising:
any one or more of a flow meter for measuring a flow rate of water injected by the endoscope, a tank in which water injected by the endoscope is stored, a weight meter for measuring a weight of the tank, a timer for measuring a water injection time by the endoscope, and an input device for inputting a water injection amount,
wherein the processor detects the amount of water injected from the distal end of the insertion part of the endoscope using at least one of a water flow rate measurement result of the flow meter, a weight measurement result of the weight meter, a time measurement result of the timer, and the water injection amount input through the input device.

9. The endoscopic diagnostic apparatus according to claim 1,
wherein the processor changes a parameter used to detect the volume of the internal space of the scope hood according to at least one of the model of the endoscope or the model of the scope hood.

10. The endoscopic diagnostic apparatus according to claim 9, further comprising:
any one or more of a flow meter for measuring a flow rate of water injected by the endoscope, a tank in which water injected by the endoscope is stored, a weight meter for measuring a weight of the tank, a timer for measuring a water injection time by the endoscope, and an input device for inputting a water injection amount,
wherein the processor detects the amount of water injected from the distal end of the insertion part of the endoscope using at least one of a water flow rate measurement result of the flow meter, a weight measurement result of the weight meter, a time measurement result of the timer, and the water injection amount input through the input device.

11. The endoscopic diagnostic apparatus according to claim 1, further comprising:
any one or more of a flow meter for measuring a flow rate of water injected by the endoscope, a tank in which water injected by the endoscope is stored, a weight meter for measuring a weight of the tank, a timer for measuring a water injection time by the endoscope, and an input device for inputting a water injection amount,
wherein the processor detects the amount of water injected from the distal end of the insertion part of the endoscope using at least one of a water flow rate measurement result of the flow meter, a weight measurement result of the weight meter, a time measurement result of the timer, and the water injection amount input through the input device.

12. The endoscopic diagnostic apparatus according to claim 1, further comprising:
any one or more of a display device for displaying the volume of the lesion part detected by the processor or outputting a warning corresponding to the volume of the lesion part detected by the processor, and a memory for recording the volume of the lesion part detected by the processor.

13. The endoscopic diagnostic apparatus according to claim 1,
wherein the processor is further configured to output a warning in a case where the water injection amount detected by the processor exceeds the volume of the internal space of the scope hood detected by the processor.

\* \* \* \* \*